United States Patent [19]

Ren

[11] Patent Number: 4,737,497

[45] Date of Patent: Apr. 12, 1988

[54] BIS-DIOXOPIPERAZINE DERIVATIVES, ANTITUMOR AGENTS COMPRISING THEM AND COMPOSITIONS CONTAINING THEM

[75] Inventor: Yun-feng Ren, New Rochelle, N.Y.

[73] Assignee: Zenyaki Kogyo Kabushiki Kaisha, Tokyo, Japan

[21] Appl. No.: 596,839

[22] Filed: Apr. 4, 1984

[30] Foreign Application Priority Data

Apr. 12, 1983 [JP] Japan ................................ 58-64368
Jul. 20, 1983 [JP] Japan ............................... 58-132657
Sep. 26, 1983 [JP] Japan ............................... 58-177703

[51] Int. Cl.$^4$ ................. A61K 31/435; A61K 31/535; A61K 31/54; C07D 413/14
[52] U.S. Cl. .................................... 514/227; 544/121; 544/60; 544/8; 544/120; 544/372; 544/385
[58] Field of Search ............... 544/106, 114, 119, 121, 544/359, 369, 385, 60; 514/252, 222, 227

[56] References Cited

FOREIGN PATENT DOCUMENTS 0055017 4/1967 German Democratic Rep. ..................................... 548/385

OTHER PUBLICATIONS

Herman et al; CA 98:118919h (4/11/83) Biological Prop. of ICRF-159 and Related Compounds.
Zhang et al: CA 94:132202t (1980) Pharmacological Studies in Bimolane—A New Antineoplastic Agent.
Saikawa et al, CA 92:41991s-2,3-Dioxopiperazinl Derivatives, (1980).
Saikawa et al., CA 92:41992t, 1,4 Distributed 2,3-Dioxopiperizines (1980).

Primary Examiner—Richard L. Raymond
Assistant Examiner—D. Dinner
Attorney, Agent, or Firm—Scrivener and Clarke

[57] ABSTRACT

Disclosed are novel bis-dioxopiperazine derivatives, process for their preparation, antitumor agents comprising them and compositions containing them.

The bis-dioxopiperazine derivatives are represented by the following general formula (I):

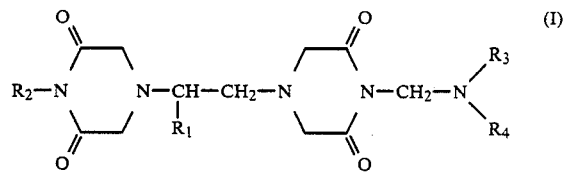

wherein $R_1$ represents a hydrogen atom or a lower alkyl group having 1 to 4 carbon atoms; $R_2$ represents a hydrogen atom or a group of

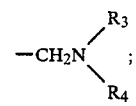

$R_3$ and $R_4$, which are respectively independent and are the same or different, represent respectively a lower alkyl group having 1 to 4 carbon atoms, a cycloalkyl group having 3 to 7 carbon atoms or a heterocyclic radical selected from the group consisting of substituted or unsubstituted piperidino, substituted or unsubstituted piperazino, substituted or unsubstituted morpholino and substituted or unsubstituted thiomorpholino, or $R_3$ and $R_4$ are bonded together to form a group of

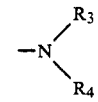

which represents a cyclic amino group selected from the group consisting of substituted or unsubstituted pyrrolidino, substituted or unsubstituted piperidino, substituted or unsubstituted piperazino, substituted or unsubstituted morpholino, substituted or unsubstituted thiomorpholino and substituted or unsubstituted thiadiazino; and the substituents of the heterocyclic radical and the cyclic amino group are selected from the group consisting of a lower alkyl group having 1 to 4 carbon atoms, oxo and phenyl, said cyclic amino group being not morpholino when $R_1$ is a hydrogen atom and $R_2$ is the group of

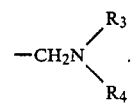

3 Claims, No Drawings

BIS-DIOXOPIPERAZINE DERIVATIVES, ANTITUMOR AGENTS COMPRISING THEM AND COMPOSITIONS CONTAINING THEM

BACKGROUND OF THE INVENTION

The present invention relates to novel bis-dioxopiperazine derivatives, process for their preparation, antitumor agents comprising them and compositions containing them.

Bis-dioxopiperazine derivatives of the present invention are compounds represented by the following general formula (I):

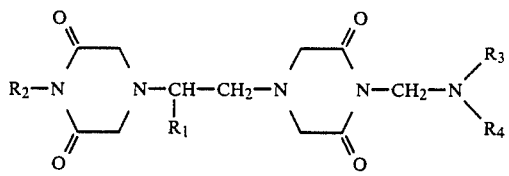

wherein $R_1$ represents a hydrogen atom or a lower alkyl group having 1 to 4 carbon atoms; $R_2$ represents a hydrogen atom or a group of

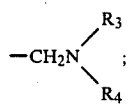

$R_3$ and $R_4$, which are respectively independent and are the same or different, represent respectively a lower alkyl group having 1 to 4 carbon atoms, a cycloalkyl group having 3 to 7 carbon atoms or a heterocyclic radical selected from the group consisting of substituted or unsubstituted piperidino, substituted or unsubstituted piperazino, substituted or unsubstituted morpholino and substituted or unsubstituted thiomorpholino, or $R_3$ and $R_4$ are bonded together to form a group of

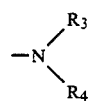

which represents a cyclic amino group selected from the group consisting of substituted or unsubstituted pyrrolidino, substituted or unsubstituted piperidino, substituted or unsubstituted piperazino, substituted or unsubstituted morpholino, substituted or unsubstituted thiomorpholino and substituted or unsubstituted thiadiazino; and the substituents of the heterocyclic radical and the cyclic amino group are selected from the group consisting of a lower alkyl group having 1 to 4 carbon atoms, oxo and phenyl, said cyclic amino group being not morpholino when $R_1$ is a hydrogen atom and $R_2$ is the group of

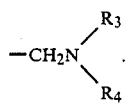

Several kinds of bis-dioxopiperazine derivatives have already been reported, especially 1,2-bis(4-morpholinomethyl-3,5-dioxopiperazin-1-yl)-ethane is known as an analogue of the compounds which the present invention concerns and its clinical efficacy as an antitumor and radio-potentiative agent was already evaluated (see Abstract, 8th International Congress of Pharmacology p441, 1981).

Based on the attractive biological activity of the known bis-dioxopiperazine derivatives, I, the inventor further carried out the synthetic study on these derivatives and found that the aforementioned bis-dioxopiperazine derivatives of the general formula (I) exhibit a broader spectrum of antitumor activity and anti-metastatic activity, thus accomplishing the present invention.

DETAILED DESCRIPTION OF THE INVENTION

Bis-dioxopiperazine derivatives of the present invention are represented by the aforementioned general formula (I) in which $R_1$ represents a hydrogen atom or a lower alkyl group having 1 to 4 carbon atoms. The lower alkyl group is selected from groups having a normal or branched carbon chain such as methyl, ethyl, n-propyl, isopropyl, n-butyl, isobutyl and tert-butyl; especially methyl group is preferred.

$R_2$ represents a hydrogen atom or a group of

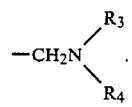

$R_3$ and $R_4$, which are independent and are the same or different, represent respectively a lower alkyl group having 1 to 4 carbon atoms, a cycloalkyl group having 3 to 7 carbon atoms or a heterocyclic radical selected from the group consisting of substituted or unsubstituted piperidino, substituted or unsubstituted piperazino, substituted or unsubstituted morpholino and substituted or unsubstituted thiomorpholino; or, $R_3$ and $R_4$ are bonded together to form a group of

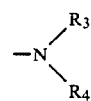

which represents a cyclic amino group selected from the group consisting of substituted or unsubstituted pyrrolidino, substituted or unsubstituted piperidino, substituted or unsubstituted piperazino, substituted or unsubstituted morpholino, substituted or unsubstituted thiomorpholino and substituted or unsubstituted thiadiazino. The substituents of the heterocyclic radical and the cyclic amino group are selected from the group consisting of a lower alkyl group having 1 to 4 carbon atoms, oxo and phenyl. Said cyclic amino group is not morpholino when $R_1$ is a hydrogen atom and $R_2$ is the group of

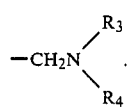

When $R_3$ and $R_4$ are respectively independent, the lower alkyl group having 1 to 4 carbon atoms is selected from groups having a normal or branched carbon chain such as methyl, ethyl, n-propyl, isopropyl and n-butyl; the cycloalkyl group having 3 to 7 carbon atoms is for example cyclopentyl or cyclohexyl. The lower alkyl group having 1 to 4 carbon atoms which is the substituent of the heterocyclic radical and the cyclic amino group is selected from groups having a normal or branched carbon chain such as methyl, ethyl, n-propyl, isopropyl and n-butyl.

When in the formula (I) the carbon atom to which $R_1$ is bonded is an asymmetric carbon atom, optical isomers, i.e., d-form and l-form are also involved in the present invention as well as the corresponding dl-form.

The compounds according to the present invention are for example as follows:

dl-form, d-form and l-form of 1-(4-morpholinomethyl-3,5-dioxopiperazin-1-yl)-2-(3,5-dioxopiperazin-1-yl)-propane dl-form, d-form and l-form of 1-(4-thiomorpholinomethyl-3,5-dioxopiperazin-1-yl)-2-(3,5-dioxopiperazin-1-yl)-propane dl-form, d-form and l-form of 1-[4-(N-phenylpiperazinomethyl)-3,5-dioxopiperazin-1-yl]-2-(3,5-dioxopiperazin-1-yl)-propane dl-form, d-form and l-form of 1-[4-(3,5-dimethylpiperidinomethyl)-3,5-dioxopiperazin-1-yl]-2-(3,5-dioxopiperazin-1-yl)-propane dl-form, d-form and l-form of 1-[4-(N-methylpiperazinomethyl)-3,5-dioxopiperazin-1-yl]-2-(3,5-dioxopiperazin-1-yl)-propane 1,2-bis(4-diethylaminomethyl-3,5-dioxopiperazin-1-yl)-ethane 1,2-bis(4-diisopropylaminomethyl-3,5-dioxopiperazin-1-yl)-ethane 1,2-bis(4-dicyclohexylaminomethyl-3,5-dioxopiperazin-1-yl)-ethane 1,2-bis[4-[N-methyl-N-piperidinoaminomethyl)-3,5-dioxopiperazin-1-yl]-ethane 1,2-bis[4-(N-methyl-N-morpholinoaminomethyl)-3,5-dioxopiperazin-1-yl]-ethane dl-form, d-form and l-form of 1,2-bis(4-diisopropylaminomethyl-3,5-dioxopiperazin-1-yl)-propane dl-form, d-form and l-form of 1,2-bis(4-dicyclohexylaminomethyl-3,5-dioxopiperazin-1-yl)-propane 1,2-bis(4-pyrrolidinomethyl-3,5-dioxopiperazin-1-yl)-ethane 1,2-bis(4-piperidinomethyl-3,5-dioxopiperazin-1-yl)-ethane 1,2-bis[4-(3,5-dimethylpiperidinomethyl)-3,5-dioxopiperazin-1-yl]-ethane 1,2-bis[4-(4-phenylpiperidinomethyl)-3,5-dioxopiperazin-1-yl]-ethane 1,2-bis[4-(N-methylpiperazinomethyl)-3,5-dioxopiperazin-1-yl]-ethane 1,2-bis[4-(N-phenylpiperazinomethyl)-3,5-dioxopiperazin-1-yl]-ethane 1,2-bis(4-thiomorpholinomethyl-3,5-dioxopiperazin-1-yl)-ethane 1,2-bis[4-(1,1-dioxoperhydro-1,2,4-thiadiazin-4-yl)methyl-3,5-dioxopiperazin-1-yl]-ethane dl-form, d-form and l-form of 1,2-bis(4-piperidinomethyl-3,5-dioxopiperazin-1-yl)-propane dl-form, d-form and l-form of 1,2-bis[4-(3,5-dimethylpiperidinomethyl)-3,5-dioxopiperazin-1-yl]-propane dl-form, d-form and l-form of 1,2-bis[4-(N-methylpiperazinomethyl)-3,5-dioxopiperazin-1-yl]-propane dl-form, d-form and l-form of 1,2-bis[4-(N-phenylpiperazinomethyl)-3,5-dioxopiperazin-1-yl]-propane dl-form, d-form and l-form of 1,2-bis(4-morpholinomethyl-3,5-dioxopiperazin-1-yl)-propane dl-form, d-form and l-form of 1,2-bis(4-thiomorpholinomethyl-3,5-dioxopiperazin-1-yl)-propane dl-form, d-form and l-form of 1,2-bis(4-pyrrolidinomethyl-3,5-dioxopiperazin-1-yl)-propane dl-form, d-form and l-form of 1,2-bis[4-(1,1-dioxoperhydro-1,2,4-thiadiazin-4-yl)methyl-3,5-dioxopiperazin-1-yl]-propane dl-form, d-form and l-form of 1,2-bis(4-morpholinomethyl-3,5-dioxopiperazin-1-yl)-n-butane dl-form, d-form and l-form of 1,2-bis(4-morpholinomethyl-3,5-dioxopiperazin-1-yl)-n-pentane dl-form, d-form and l-form of 1,2-bis(4-morpholinomethyl-3,5-dioxopiperazin-1-yl)-n-hexane Compounds of general formula (I) according to the present invention are prepared by a preparation method of the present invention which is characterized by reacting a compound represented by the following general formula (II)

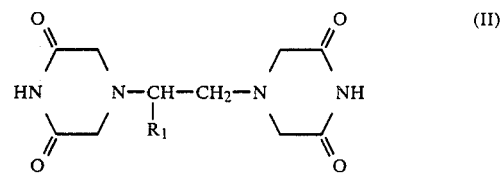

wherein $R_1$ is as defined above, with formaldehyde and amine represented by the following general formula (III)

wherein $R_3$ and $R_4$ are as defined above.

Examples of the amine of the formula (III) are as follows: When $R_3$ and $R_4$ are respectively independent, such amine may be di-lower-alkyl-amine such as dimethylamine, diethylamine and diisopropylamine, dicycloalkylamine such as dicyclopentylamine and dicyclohexylamine, N-methyl-N-piperidinoamine, N-methyl-N-piperazinoamine, N-methyl-N-morpholinoamine or N-methyl-N-thiomorpholinoamine; when $R_3$ and $R_4$ are bonded together, such amine may be a cyclic amine such as pyrrolidine, piperidine, 3,5-dimethylpiperidine, 4-phenylpiperidine, N-methylpiperazine, N-phenylpiperazine, morpholine, thiomorpholine or 1,1-dioxoperhydro-1,2,4-thiadiazine.

In the aforementioned reaction, when $R_2$ in the formula (I) is a hydrogen atom, 0.8 to 1.1 equivalent molar amounts of formaldehyde and amine of the formula (III) should be used to 1 molar amount of the starting material of the formula (II), respectively.

Reaction temperature can be selected at $-20°$ to $120°$ C., preferably at $0°$ to $30°$ C., and reaction time may be 0.5 to 40 hours which depends on reaction temperature. As for the reaction solvent, a polar solvent or mixture of polar solvents may be used. Such polar solvent is for example N,N-dimethylformamide (DMF), acetonitrile, ethyl acetate, methanol, ethanol or butanol.

When $R_2$ is the group of

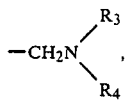

at least 2 equivalent molar amounts of formaldehyde and amine of the formula (III) should be used to 1 molar amount of the starting material of the formula (II), respectively.

Reaction temperature can be selected at 30° to 200° C., preferably at 50° to 170° C., and reaction time may be 0.1 to 3.0 hours. As for the reaction solvent, a polar solvent or a mixture of polar solvents may be used. Such polar solvent is for example DMF, 1,3-dimethyl-2-imidazolidinone (DMI), N-methylpyrrolidone (NMP), methanol, ethanol, propanol, chloroform, dichloromethane, tetrahydrofuran (THF) or dioxane.

The compound of the formula (I) in which $R_2$ is a hydrogen atom may also be prepared by solvolyzing with a protic polar solvent the compound of the formula (I) in which $R_2$ is the group of

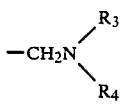

and which is prepared by the aforementioned reaction. Such protic polar solvent is for example a lower alcohol such as methanol, ethanol of n-butanol or water.

Reaction temperature can be selected at −20° to 60° C., preferably at 0° to 35° C., and reaction time may be 0.5 to 5 hours. As for the reaction solvent, an aprotic polar solvent such as DMF, pyridine, ethyl acetate or chloroform may be used in combination with the aforementioned protic polar solvent.

The compounds of the formula (II) which are the starting materials in a process of the present invention are known compounds and can be prepared according to the method described in British Patent Specification No. 1,234,935.

Next, described are the antitumor activities and the toxicities of bis-dioxopiperazine derivatives which the present invention concerns and which are obtained by the aforementioned preparation process.

The antitumor activities of the compounds of the present invention were verified by the growth inhibition or the increase of life span in experimental animals with syngenic tumor such as Lewis lung carcinoma, B-16 melanoma, Colon adenocarcinoma No. 38 and P388 leukemia and with allogenic tumors such as Sarcoma 37 and Hepatoma 22 as shown below.

(1) Animal test on Lewis lung carcinoma

The treated group to which the compound of the present invention was administered consisted of seven mice, while the control group consisted of ten mice. Six weeks old male mice [BDF$_1$ (C57BL/6×DBA/2), 25±2 g of body weight] were employed as host animals.

Tumor cells (5×10$^5$) of Lewis lung carcinoma were transplanted subcutaneously in inguinal region of each mouse. The treatment began one day after the transplantation and the prescribed dose of each test compound was administered orally to the mice once a day for 8 days.

On the 20th day after the transplantation, the tumors of all the mice were excised and weighed. Antitumor activity of the test compound was evaluated by the rate of growth inhibition (G.I.%) which was calculated with the following formula.

$$G.I. (\%) = \left(1 - \frac{T}{C}\right) \times 100$$

T: mean tumor weight of treated mice
C: mean tumor weight of control mice
The results obtained are shown in Table 1.

TABLE 1

| Results of Growth Inhibition Test on Lewis Lung Carcinoma | | |
|---|---|---|
| Test Compound | Daily Dose (mg/kg) | G.I. (%) |
| dl-1,2-bis(4-morpholinomethyl-3,5-dioxopiperazin-1-yl)-propane | 60 | 89.3 |
| 1,2-bis[4-(3,5-dimethylpiperidinomethyl)-3,5-dioxopiperazin-1-yl]-ethane | 60 | 67.2 |
| 1,2-bis[4-(N—phenylpiperazinomethyl)-3,5-dioxopiperazin-1-yl]-ethane | 60 | 78.9 |
| dl-1,2-bis[4-(3,5-dimethylpiperidinomethyl)-3,5-dioxopiperazin-1-yl]-propane | 60 | 77.4 |
| dl-1,2-bis[4-(N—methylpiperazinomethyl)-3,5-dioxopiperazin-1-yl]-propane | 60 | 53.5 |
| dl-1,2-bis[4-(N—phenylpiperazinomethyl)-3,5-dioxopiperazin-1-yl]-propane | 40 | 89.0 |
| dl-1-(4-morpholinomethyl-3,5-dioxopiperazin-1-yl)-2-(3,5-dioxopiperazin-1-yl)-propane | 40 | 83.9 |
| dl-1-[4-(N—phenylpiperazinomethyl)-3,5-dioxopiperazin-1-yl]-2-(3,5-dioxopiperazin-1-yl)-propane | 40 | 76.2 |
| 1,2-bis(4-morpholinomethyl-3,5-dioxopiperazin-1-yl)-ethane (known compound) | 60 | 22.6 |

Against Lewis lung carcinoma, the rate of growth inhibition of the compound which the present invention concerns was superior to that of the comparative compound. In addition, it was confirmed that the compound of the present invention suppressed the metastasis of Lewis lung carcinoma significantly as compared with control group.

(2) Animal test on B-16 melanoma

The treated group to which the compound of the present invention was administered consisted of seven mice, while the control group consisted of ten mice. Six weeks old male mice [BDF$_1$ (C57BL/6×DBA/2), 25+2 g of body weight] were employed as host animals.

Tumor cells (5×10$^5$) of B-16 melanoma were transplanted subcutaneously in inguinal region of each mouse. The treatment began one day after the transplantation and the prescribed dose of each test compound was administered orally to the mice once a day for 8 days.

On the 20th day after the transplantation, the tumors of all the mice were excised and weighed. Antitumor activity of the test compound was evaluated by the rate of growth inhibition (G.I.%) which was calculated in the same manner as used in the animal test on Lewis lung carcinoma. The results obtained are shown in Table 2.

TABLE 2

| Results of Growth Inhibition Test on B-16 Melanoma | | |
|---|---|---|
| Test Compound | Daily Dose (mg/kg) | G.I. (%) |
| dl-1,2-bis(4-morpholinomethyl-3,5- | 60 | 93.8 |

TABLE 2-continued

Results of Growth Inhibition Test on B-16 Melanoma

| Test Compound | Daily Dose (mg/kg) | G.I. (%) |
|---|---|---|
| dioxopiperazin-1-yl)-propane | | |
| 1,2-bis[4-(3,5-dimethylpiperidinomethyl)-3,5-dioxopiperazin-1-yl]-ethane | 60 | 68.9 |
| 1,2-bis[4-(N—phenylpiperazinomethyl)-3,5-dioxopiperazin-1-yl]-ethane | 60 | 91.9 |
| 1,2-bis(4-thiomorpholinomethyl-3,5-dioxopiperazin-1-yl)-ethane | 60 | 73.5 |
| dl-1,2-bis[4-(3,5-dimethylpiperidinomethyl)-3,5-dioxopiperazin-1-yl]-propane | 60 | 91.2 |
| dl-1,2-bis[4-(N—phenylpiperazinomethyl)-3,5-dioxopiperazin-1-yl]-propane | 20 | 71.0 |
| dl-1,2-bis(4-thiomorpholinomethyl-3,5-dioxopiperazin-1-yl)-propane | 40 | 77.5 |
| dl-1-(4-morpholinomethyl-3,5-dioxopiperazin-1-yl)-2-(3,5-dioxopiperazin-1-yl)-propane | 40 | 76.1 |
| dl-1-[4-(N—phenylpiperazinomethyl)-3,5-dioxopiperazin-1-yl]-2-(3,5-dioxopiperazin-1-yl)-propane | 20 | 60.8 |
| 1,2-bis(4-morpholinomethyl-3,5-dioxopiperazin-1-yl)-ethane (known compound) | 60 | 48.9 |

Against B-16 melanoma, the rate of growth inhibition of the compound which the present invention concerns was superior to that of the comparative compound.

(3) Animal test on Colon adenocarcinoma No. 38

The treated group to which the compound of the present invention was administered consisted of seven mice, while the control group consisted of ten mice. Six weeks old male mice [BDF$_1$ (G57BL/6×DBA/2), 25±2 g of body weight] were employed as hosts animals.

Tumor cells (40 mg of fragment) of Colon adenocarcinoma No. 38 were transplanted subcutaneously in inguinal region of each mouse. The treatment began one day after the transplantation and the prescribed dose of each test compound was administered orally to the mice once a day for 8 days.

On the 30th day after the transplantaion, the tumors of all the mice were excised and weighed. Antitumor activity of the test compound was evaluated by the rate of growth inhibition (G.I.%) which was calculated in the same manner as used in the animal test on Lewis lung carcinoma. The results obtained are shown in Table 3.

TABLE 3

Results of Growth Inhibition Test on Colon Adenocarcinoma No. 38

| Test Compound | Daily Dose (mg/kg) | G.I. (%) |
|---|---|---|
| dl-1,2-bis(4-morpholinomethyl-3,5-dioxopiperazin-1-yl)-propane | 60 | 91.6 |
| 1,2-bis[4-(3,5-dimethylpiperidinomethyl)-3,5-dioxopiperazin-1-yl]-ethane | 60 | 83.1 |
| 1,2-bis[4-(N—phenylpiperazinomethyl)-3,5-dioxopiperazin-1-yl]-ethane | 60 | 97.9 |
| dl-1-(4-morpholinomethyl-3,5-dioxopiperazin-1-yl)-2-(3,5-dioxopiperazin-1-yl)-propane | 40 | 74.1 |
| dl-1-[4-(N—phenylpiperazinomethyl)-3,5-dioxopiperazin-1-yl]-2-(3,5-dioxopiperazin-1-yl)-propane | 40 | 93.5 |
| 1,2-bis(4-morpholinomethyl-3,5-dioxopiperazin-1-yl)-ethane (known compound) | 60 | 72.8 |

Against Colon adenocarcinoma No. 38, the rate of growth inhibition of the compound which the present invention concerns was equivalent to or superior to the comparative compound.

(4) Animal test on Sarcoma 37

The treated group to which the compound of the present invention was administered consisted of eight mice, while the control group consisted of sixteen mice. Four weeks old female mice (K-M, 20±2 g of body weight) were employed as host animals.

Tumor cells (0.2 ml of 1:5 suspension) of Sarcoma 37 were transplanted subcutaneously in the flank of each mouse. The treatment began one day after the transplantation and the prescribed dose (1.56–50 mg/kg) of dl-1,2-bis(4-morpholinomethyl-3,5-dioxopiperazin-1-yl)-propane was administered intraperitoneally (i.p.) or orally (p.o.) to the mice once a day for 10 days.

On the 12th day after the transplantation, the tumors of all the mice were excised and weighed. Antitumor activity of the test compound was evaluated by the rate of growth inhibition (G.I.%) which was calculated in the same manner as used in the animal test on Lewis lung carcinoma. The results obtained are shown in Table 4.

TABLE 4

Results of Growth Inhibition Test on Sarcoma 37

| Daily Dose (mg/kg) | G.I. (%) i.p. | G.I. (%) p.o. |
|---|---|---|
| 1.56 | 33.2 | — |
| 3.12 | 56.1 | 39.3 |
| 6.25 | 72.7 | 68.8 |
| 12.5 | 82.4 | 94.2 |
| 25 | 94.6 | 100 |
| 50 | 100 | — |

The ED$_{50}$s were determined as 3.1 mg/kg (i.p.) and 4.3 mg/kg (p.o.).

(5) Animal test on Hepatoma 22

The treated group to which the compound of the present invention was administered consisted of ten mice, while the control group consisted of twenty mice. Four weeks old female mice (K-M, 20±2 g of body weight) were employed as host animals.

Tumor cells (a 2 mm$^3$ fragment) of Hepatoma 22 were transplanted subcutaneously in the flank of each mouse. The treatment began one day after the transplantation and the prescribed dose of the test compound was administered orally to the mice once a day for 9 days.

On the 12th day after the transplantation, the tumors of all the mice were excised and weighed. Antitumor activity of the test compound was evaluated by the rate of growth inhibition (G.I.%) which was calculated in the same manner as used in the animal test on Lewis lung carcinoma. The results obtained are shown in Table 5.

TABLE 5

Results of Growth Inhibition Test on Hepatoma 22

| Test Compound | Daily Dose (mg/kg) | G.I. (%) |
|---|---|---|
| dl-1,2-bis(4-morpholinomethyl-3,5-dioxopiperazin-1-yl)-propane | 25 | 42.7 |
| 1,2-bis(4-morpholinomethyl-3,5-dioxopiperazin-1-yl)-ethane (known compound) | 25 | 12.9 |

Against Hepatoma 22, the rate of growth inhibition of the compound which the present invention concerns was superior to that of a comparative compound.

In addition, the compounds of the present invention which are used in the aforementioned animal test on B-16 melanoma exhibited effectiveness against the other syngenic experimental tumor (P388 leukemia).

The toxicities of the compounds which the present invention concerns were examined by the following tests.

(6) Animal test on acute toxicity

The test group to which the compound of the present invention was administered consisted of ten mice. Five weeks old male mice (ddY, 23±2 g of body weight) were employed as test animals.

These animals were intraperitoneally given the test compound which was suspended in the saline solution containing carboxymethyl cellulose (CMC) by 0.5% and were observed for 14 days successively, and $LD_{50}$ value of acute toxicity was determined by Litchfield-Wilcoxon method. The results obtained are shown in Table 6.

TABLE 6

| Results of Acute Toxicity Test | |
|---|---|
| Test Compound | $LD_{50}$(mg/kg) |
| dl-1,2-bis(4-morpholinomethyl-3,5-dioxopiperazin-1-yl)-propane | 255 |
| 1,2-bis[4-(3,5-dimethylpiperidinomethyl)-3,5-dioxopiperazin-1-yl]-ethane | 400–500 |
| 1,2-bis[4-(N—phenylpiperazinomethyl)-3,5-dioxopiperazin-1-yl]-ethane | 200–300 |
| dl-1,2-bis[4-(N—methylpiperazinomethyl)-3,5-dioxopiperazin-1-yl]-propane | 300–400 |
| dl-1,2-bis[4-(N—phenylpiperazinomethyl)-3,5-dioxopiperazin-1-yl]-propane | 100 |
| dl-1,2-bis(4-thiomorpholinomethyl)-3,5-dioxopiperazin-1-yl)-propane | 330 |
| dl-1-[4-(N—phenylpiperazinomethyl)-3,5-dioxopiperazin-1-yl]-2-(3,5-dioxopiperazin-1-yl)-propane | more than 350 |
| 1,2-bis(4-morpholinomethyl-3,5-dioxopiperazin-1-yl)-ethane (known compound) | 280 |

(7) Animal test on subacute toxicity

The test group to which the compound of the present invention was administered consisted of ten mice, while the control group consisted of ten mice. Four weeks old female mice (K-M, 20±2 g of body weight) were employed as test animals.

These animals were intraperitoneally given the test compound which was suspended in the aqueous solution containing CMC by 0.5% once a day for 8 days, and were observed for 14 days successively. $LD_{50}$ value of the subacute toxicity was determined by the Bliss-Finney statistical method. The results obtained are shown in Table 7.

TABLE 7

| Results of Subacute Toxicity Test | |
|---|---|
| Test Compound | $LD_{50}$(mg/kg) |
| dl-1,2-bis(4-morpholinomethyl-3,5-dioxopiperazin-1-yl)-propane | 177.8 |
| 1,2-bis(4-morpholinomethyl-3,5-dioxopiperazin-1-yl)-ethane (known compound) | 59.3 |

The following descriptions are given for the administration routes, pharmaceutical forms, and doses when bis-dioxopiperazine derivatives of the present invention are applied to human.

The compounds of the present invention may be administered orally in forms such as tablets, coatings, powders, granules, capsules and syrups. They may also be administered parenterally in forms such as an injection which may include dissolvable freeze-drying form, and suppositories.

In the preparation of these forms, pharmaceutically acceptable diluent bases, binders, disintegrators, lubricants, suspensions, emulsifiers, antiseptics, stabilizers and dispersing agents, for example, lactose, sucrose, starch, dextrin, crystalline cellulose, kaolin, calcium carbonate, talc, magnesium stearate, distilled water and physiological saline solution may be used.

Although the daily doses of these compounds may be varied according to the conditions, ages and body weights of patients to be treated, the daily doses to adult humans may normally fall within the range of 50 to 3000 mg and preferably 500 to 1000 mg and may be divided into two or three portions.

From the above description, the compounds of the present invention are not only expected useful as antitumor agents and radio-potentiative agents similarly to the known compound of 1,2-bis(4-morpholinomethyl-3,5-dioxopiperazin-1-yl)-ethane, but also expected to have a broader antitumor spectrum and more excellent antitumor activity from the results of aforementioned antitumor tests as well as to have lower toxicity than that of the comparative compound.

The preparation method of the compounds (I) claimed in the present invention consists of relatively simple steps in high yields and is suitable for industrial production.

The invention is illustrated by the following examples, but it should be noted that the present invention is not limited to these examples.

EXAMPLE 1 dl-1,2-Bis(4-morpholinomethyl-3,5-dioxopiperazin-1-yl)-propane

A mixture of dl-1,2-bis(3,5-dioxopiperazin-1-yl)-propane (26.8 g, 0.1 mole), morpholine (27 ml, 0.3 mole) and absolute ethanol (100 ml) was heated to reflux. To the mixture, 37% aqueous formaldehyde solution (27 ml) was added gradually and then the reaction mixture was refluxed for further 15 minutes. The cooled mixture was filtered and the filtrate was allowed to stand in the refrigerator. Then resulting white crystals were collected and washed with ethyl acetate to give the titled compound (39.6 g; yield 84.9%).

Melting Point: 163° to 165° C. (recrystallized from ethyl acetate).

Elementary Analysis (%). Calculated for $C_{21}H_{34}N_6O_6$: C 54.06; H 7.35; N 18.01. Found: C 54.28; H 7.58; N 18.05.

Infrared Absorption (IR) Spectrum (KBr) cm$^{-1}$: 1735, 1687.

Nuclear Magnetic Resonance (NMR) Spectrum (CDCl$_3$·100 MHz) δppm:

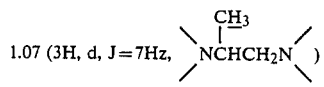

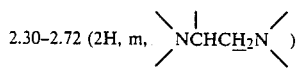

-continued

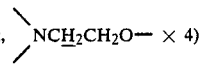
2.60 (8H, t, J=5Hz, >NCH₂CH₂O— ×4)

2.80–3.06 (1H, m, >NCHCH₂N< )

3.47, 3.52 (8H, s, >NCH₂CO—×4) 3.65 (8H, t, J=5 Hz, >NCH₂CH₂O—×4) 4.71 (4H, s, >NCH₂N<×2)

Mass Spectrum (m/e): 466 (M+), 379 (M+−87), 365 (M+−101). Solubility in Water: 20 mg/ml (25° C.).

EXAMPLE 2 dl-1,2-Bis(4-morpholinomethyl-3,5-dioxopiperazin-1-yl)-propane was also obtained in a 80% yield by the procedure of Example 1 with using the mixture of DMF (27 ml) and absolute ethanol (27 ml) as solvent.

EXAMPLE 3

1,2-Bis(4-thiomorpholinomethyl-3,5-dioxopiperazin-1-yl)-ethane

A mixture of thiomorpholine (1.6 g, 15.6 m mole), DMF (20 ml), absolute ethanol (5 ml) and 1,2-bis(3,5-dioxopiperazin-1-yl)-ethane (2.0 g, 7.87 m mole) was stirred at 150° C. for ten minutes. The mixture was treated with 37% aqueous formaldehyde solution (1.34 ml) and was stirred at the same temperature for further 1.5 hours. Then, the reaction mixture was filtered while it was still hot, and the filtrate was condensed under a reduced pressure. The resulting crystals were collected and were fully washed with ether to give the titled compound (2.06 g; yield 54%).

Melting Point: 183° to 185° C.

Elementary Analysis (%). Calculated for C₂₀H₃₂N₆S₂O₄: C 49.57; H 6.66; N 17.34; S 13.23. Found: C 49.37; H 6.52; N 17.21; S 13.36.

IR Spectrum (KBr) cm⁻¹: 2930, 2900, 2825, 1730, 1680.

NMR Spectrum (CDCl₃) δppm: 2.59–2.63 (8H, m, >NCH₂CH₂S—×4); 2.67 (4H, s, >NCH₂CH₂N<); 2.87–2.89 (8H, m, >NCH₂CH₂S—×4); 3.48 (8H, s, >NCH₂CO—×4); 4.75 (4H, s, >NCH₂N<×2).

In accordance with the procedure of Example 3, the following compounds were obtained from the corresponding starting materials.

1,2-Bis[4-(3,5-dimethylpiperidinomethyl)-3,5-dioxopiperazin-1-yl]-ethane (yield 37%)

Melting Point: 174° to 176° C.

Elementary Analysis (%). Calculated for C₂₆H₄₄N₆O₄: C 61.88; H 8.79; N 16.65. Found: C 61.78; H 8.67; N 16.60.

IR Spectrum (KBr) cm⁻¹: 2950, 2790, 1730, 1680.

1,2-Bis[4-(N-phenylpiperazinomethyl)-3,5-dioxopiperazin-1-yl]-ethane (yield 44%)

Melting Point: 172° to 175° C.

Elementary Analysis (%). Calculated for C₃₂H₄₂N₈O₄: C 63.77; H 7.02; N 18.59. Found: C 63.65; H 7.15; N 18.44.

IR Spectrum (KBr) cm⁻¹: 2940, 2810, 1720, 1680.

EXAMPLE 4

1,2-Bis[4-(N-methylpiperazinomethyl)-3,5-dioxopiperazin-1-yl]-ethane

A mixture of N-methylpiperazine (2.21 ml, 20 m mole), DMF (25 ml), chloroform (6 ml) and 1,2-bis(3,5-dioxopiperazin-1-yl)-ethane (2.54 g, 10 m mole) was stirred at 70° C. for ten minutes. The mixture was treated with 37% aqueous formaldehyde solution (1.62 ml) and was stirred at the same temperature for further 2 hours. Then, the same procedure as in Example 3 was made to give the titled compound (3.3 g; yield 68%).

Melting Point: 112° to 118° C. (decomp.).

IR Spectrum (KBr) cm⁻¹: 2940, 2790, 1730, 1680.

NMR Spectrum (CDCl₃) δppm: 2.27 (6H, s, >N—CH₃×2);

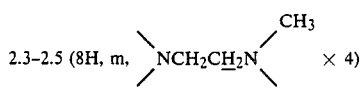
2.3–2.5 (8H, m, >NCH₂CH₂N<CH₃ ×4)

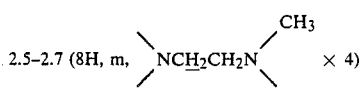
2.5–2.7 (8H, m, >NCH₂CH₂N<CH₃ ×4)

2.63 (4H, s, >NCH₂CH₂N<); 3.47 (8H, s, >NCH₂CO—×4); 4.81 (4H, s, >NCH₂N<×2).

In accordance with the procedure of Example 4, the following compounds were obtained from the corresponding starting materials.

1,2-Bis[4-(N-methyl-N-morpholinoaminomethyl)-3,5-dioxopiperazin-1-yl]-ethane (yield 80%)

Melting Point: 144° to 148° C. (decomp.).

IR Spectrum (KBr) cm⁻¹: 2950, 2850, 1730, 1680.

1,2-Bis[4-(N-methyl-N-piperidinoaminomethyl)-3,5-dioxopiperazin-1-yl]-ethane (yield 43%)

Melting Point: 102° to 105° C. (decomp.).

IR Spectrum (KBr) cm⁻¹: 2920, 2830, 2770, 1720, 1680.

EXAMPLE 5

1,2-Bis(4-pyrrolidinomethyl-3,5-dioxopiperazin-1-yl)-ethane

A mixture of pyrrolidine (1.31 ml, 15.8 m mole), DMF (20 ml), chloroform (5 ml) and 1,2-bis(3,5-dioxopiperazin-1-yl)-ethane (2.0 g, 7.87 m mole) was stirred at 70° C. for ten minutes. The mixture was treated with 37% aqueous formaldehyde solution (1.34 ml) and was stirred at the same temperature for further 30 minutes. Then, the same procedure as in Example 3 was made to give the titled compound (2.37 g; yield 71%).

Melting Point: 150° to 155° C.

IR Spectrum (KBr) cm⁻¹: 2950, 2790, 1725, 1680.

NMR Spectrum (CDCl₃) δppm:

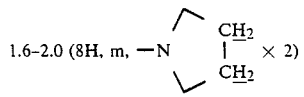
1.6–2.0 (8H, m, —N⟨CH₂/CH₂ ×2)

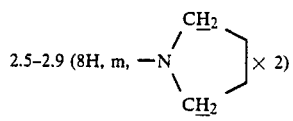

2.68 (4H, s, >NCH$_2$CH$_2$N<); 3.50 (8H, s, >NCH$_2$CO—×4); 4.87 (4H, s, >NCH$_2$N<×2).

In accordance with the procedure of Example 5, the following compounds were obtained from the corresponding starting materials.

1,2-Bis(4-piperidinomethyl-3,5-dioxopiperazin-1-yl)-ethane (yield 72%)

Melting Point: 132° to 138° C.

IR Spectrum (KBr) cm$^{-1}$: 2930, 2850, 2800, 1730, 1680.

1,2-Bis[4-(4-phenylpiperidinomethyl)-3,5-dioxopiperazin-1-yl]-ethane (yield 77%)

Melting Point: 157° to 160° C.

IR Spectrum (KBr) cm$^{-1}$: 2940, 1730, 1685.

1,2-Bis(4-diethylaminomethyl-3,5-dioxopiperazin-1-yl)-ethane (yield 14%)

Melting Point: 107° to 110.5° C.

IR Spectrum (KBr) cm$^{-1}$: 2970, 2830, 1715, 1670.

EXAMPLE 6 dl-1,2-Bis[4-(3,5-dimethylpiperidinomethyl)-3,5-dioxopiperazin-1-yl]-propane

A mixture of 3,5-dimethylpiperidine (2.8 ml, 21 m mole), DMF (15 ml), 1,4-dioxane (15 ml) and dl-1,2-bis(3,5-dioxopiperazin-1-yl)-propane (2.0 g, 7.4 m mole) was stirred at 110° C. for ten minutes. The mixture was treated with 37% aqueous fromaldehyde solution (1.32 ml) and was stirred at the same temperature for further 2 hours. Then, the same procedure as in Example 3 was made to give the titled compound (1.69 g; yield 44%).

Melting Point: 142° to 144.5° C.

Elementary Analysis (%). Calculated for C$_{27}$H$_{46}$N$_6$O$_4$: C 62.52; H 8.94; N 16.20. Found: C 62.40; H 9.08; N 16.04.

IR Spectrum (KBr) cm$^{-1}$: 2950, 2900, 2790, 1730, 1680.

EXAMPLE 7 dl-1,2-Bis[4-(N-phenylpiperazinomethyl)-3,5-dioxopiperazin-1-yl]-propane

A mixture of N-phenylpiperazine (2.9 g, 17.7 m mole), DMF (20 ml), absolute ethanol (5 ml) and dl-1,2-bis(3,5-dioxopiperazin-1-yl)-propane (2,0 g, 7.4 m mole) was stirred at 150° C. for ten minutes. The mixture was treated with 37% aqueous formaldehyde solution (1.40 ml) and was stirred at the same temperature for further 1.5 hours. Then, the same procedure as in Example 3 was made to give the titled compound (2.9 g; yield 88%).

Melting Point: 94° to 101° C.

Elementary Analysis (%). Calculated for C$_{33}$H$_{44}$N$_8$O$_4$: C 64.26; H 7.19; N 18.17. Found: C 64.20; H 7.28; N 18.02.

IR Spectrum (KBr) cm$^{-1}$: 2925, 1725, 1675.

NMR Spectrum (CDCl$_3$) δppm:

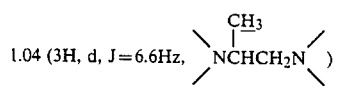

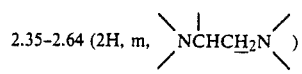

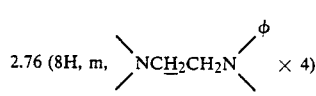

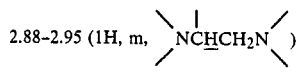

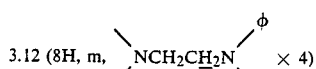

3.47, 3.51 (8H, s, >NCH$_2$CO—×4); 4.81 (4H, s, >NCH$_2$N<×2); 6.84–6.90 (6H, m, phenyl); 7.21–7.27 (4H, m, phenyl).

In accordance with the procedure of Example 7, the following compound was obtained from the corresponding starting material.

dl-1,2-Bis[4-(thiomorpholinomethyl)-3,5-dioxopiperazin-1-yl]-propane (yield 61%)

Melting Point: 140° to 143° C.

Elementary Analysis (%). Calculated for C$_{21}$H$_{34}$N$_6$S$_2$O$_4$: C 50.58; H 6.87; N 16.85; S 12.86. Found: C 50.33; H 6.95; N 16.71; S 12.66.

IR Spectrum (KBr) cm$^{-1}$: 2920, 2840, 1735, 1690.

EXAMPLE 8 dl-1,2-Bis[4-(N-methylpiperazinomethyl)-3,5-dioxopiperazin-1-yl]-propane

A mixture of N-methylpiperazine (2.21 ml, 20.0 m mole), DMF (25 ml), chloroform (6 ml) and 1,2-bis(3,5-dioxopiperazin-1-yl)-propane (2.68 g, 10.0 m mole) was stirred at 70° C. for ten minutes. The mixture was treated with 37% aqueous formaldehyde solution (1.62 ml) and was stirred at the same temperature for further 1.5 hours. Then, the same procedure as in Example 3 was made to give the titled compound (2.7 g; yield 55%).

Melting Point: 93° to 96° C.

Elementary Analysis (%). Calculated for C$_{23}$H$_{40}$N$_8$O$_4$: C 56.08; H 8.18; N 22.75. Found: C 55.82; H 8.20; N 22.60.

IR Spectrum (KBr) cm$^{-1}$: 2940, 2800, 1730, 1680.

In accordance with the procedure of Example 8, the following compound was obtained from the corresponding starting material.

dl-1,2-Bis(4-piperidinomethyl-3,5-dioxopiperazin-1-yl)-propane (yield 50%)

Melting Point: 101° to 106° C.

IR Spectrum (KBr) cm$^{-1}$: 2930, 2800, 1730, 1680.

EXAMPLE 9 dl-1-(4-Morpholinomethyl-3,5-dioxopiperazin-1-yl)-2-(3,5-dioxopiperazin-1-yl)-propane Water (200 ml) was added to dl-1,2-bis(4-morpholinomethyl-3,5-dioxopiperazin-1-yl)-propane (4.0 g) obtained in Example 1 and the mixture was stirred at room temperature for 0.5 hours. Then, the mixture was filtered and the filtrate was stirred at room temperature for further 3 hours. The reaction mixture was freezed on a dry ice-acetone bath and the freezed mixture was allowed to stand at room temperature to give an aqueous suspension. Colorless solids, which precipitated in the aqueous suspension, were collected by filtration and dried over phosphorus pentaoxide under a reduced pressure to give the titled compound (1.22 g; yield 40%).

Melting Point: 162° to 165° C.

Elementary Analysis (%). Calculated for $C_{16}H_{25}N_5O_5$: C 52.31; H 6.86; N 19.06. Found: C 52.05; H 6.95; N 19.26.

IR Spectrum (KBr) cm$^{-1}$: 2960, 2850, 2800, 1700, 1685.

NMR Spectrum (CDCl$_3$) δppm:

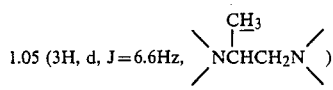
1.05 (3H, d, J=6.6Hz, )

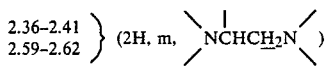
2.36–2.41
2.59–2.62 } (2H, m, )

2.56–2.59 (4H, m, morpholine)

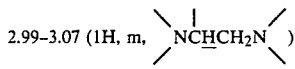
2.99–3.07 (1H, m, )

3.43–3.46 (4H, m, >NCH$_2$CO—×2); 3.48 (4H, s, >NCH$_2$CO—×2); 3.63–3.66 (4H, m, morpholine); 4.74 (2H, s, >NCH$_2$N<).

Mass spectrum (m/e): 367 (M+).

EXAMPLE 10 dl-1-(4-Thiomorpholinomethyl-3,5-dioxopiperazin-1-yl)-2-(3,5-dioxopiperazin-1-yl)-propane Water (30 ml) was added to dl-1,2-bis(4-thiomorpholinomethyl-3,5-dioxopiperazin-1-yl)-propane (0.6 g) and the suspension thus obtained was stirred at room temperature for 5 hours. Then, the precipitates thus obtained were collected and were dried under a reduced pressure. Chloroform (10 ml) was added to the dried precipitates and the whole was stirred at room temperature for 20 minutes, then was filtered. The filtration residue was dried under a reduced pressure to give the titled compound (0.2 g; yield 43%).

Melting Point: 205.5° to 208.5° C.

Elementary Analysis (%). Calculated for $C_{16}H_{25}N_5SO_4$: C 50.12; H 6.57; N 18.26; S 8.36. Found: C 50.41; H 6.40; N 18.01; S 8.16.

IR Spectrum (KBr) cm$^{-1}$: 2960, 2800, 1700, 1680.

NMR Spectrum (CDCl$_3$) δppm:

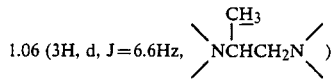
1.06 (3H, d, J=6.6Hz, )

2.39–2.45
2.60–2.67 } (6H, m, and thiomorpholine)

2.85–2.94 (4H, m, thiomorpholine)

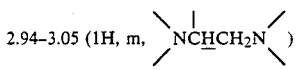
2.94–3.05 (1H, m, )

3.43–3.46 (4H, m, >NCH$_2$CO—×2); 3.46 (4H, s, >NCH$_2$CO—×2); 4.74 (2H, s, >NCH$_2$N<).

In accordance with the procedure of Example 10, the following compound was obtained from the corresponding starting material which was obtained in Example 7.

dl-1-[4-(N-Phenylpiperazinomethyl)-3,5-dioxopiperazin-1-yl]-2-(3,5-dioxopiperazin-1-yl)-propane Melting Point: 188° to 190° C.

Elementary Analysis (%). Calculated for $C_{22}H_{30}N_6O_4$: C 59.71; H 6.83; N 18.99. Found: C 59.50; H 6.99; N 18.85.

IR Spectrum (KBr) cm$^{-1}$: 2975, 2820, 1710, 1690.

NMR Spectrum (CDCl$_3$) δppm:

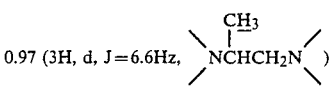
0.97 (3H, d, J=6.6Hz, )

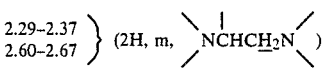
2.29–2.37
2.60–2.67 } (2H, m, )

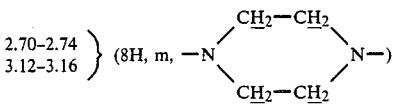
2.70–2.74
3.12–3.16 } (8H, m, )

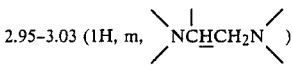
2.95–3.03 (1H, m, )

3.40–3.43 (4H, m, >NCH$_2$CO—×2); 3.49 (4H, s, >NCH$_2$CO—×2); 4.86 (2H, s, >NCH$_2$N<);

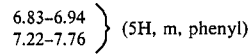
6.83–6.94
7.22–7.76 } (5H, m, phenyl)

EXAMPLE 11 dl-1-[4-(N-Phenylpiperazinomethyl)-3,5-dioxopiperazin-1-yl]-2-(3,5-dioxopiperazin-1-yl)-propane A mixture of N-phenylpiperazine (0.81 g, 5 m mole), DMF (13.4 ml), absolute ethanol (3,3 ml), 37% aqueous formaldehyde solution (0.43 ml) and dl-1,2-bis(3,5-dioxopiperazin-1-yl)-propane (1.34 g, 5 m mole) was stirred at room temperature for 48 hours. Then, the precipitates thus obtained were collected and were washed with absolute ethanol and then with ether. The washed precipitates were dried under a reduced pressure to give the titled compound (1.39 g; yield 62%). The compound obtained in this Example was proved to be identical with the compound described in Example 10 on the basis of the melting point and IR Spectrum.

What is claimed is:
1. A compound represented by the formula

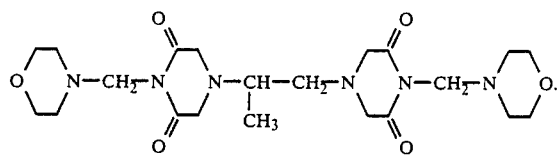
2. The dl-mixture of the compound according to claim 1.
3. A pharmaceutical composition containing a compound as described in claim 1 in an amount effective against Lewis lung carcinoma, B-16 melanoma, Colon adenocarcinoma No. 38, Sarcoma 37, Hepatoma 22 or P388 leukemia, and a pharmaceutically acceptable diluent or carrier.
* * * * *